(12) United States Patent
Sürig (10) Patent No.: US 10,539,619 B2
(45) Date of Patent: Jan. 21, 2020

(54) TESTING DEVICE AND METHOD FOR TESTING A VIBRATION MOTOR ARRANGED IN A DEVICE

(71) Applicant: Dräger Safety AG & Co. KGaA, Lübeck (DE)

(72) Inventor: Andreas Sürig, Krummesse (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 81 days.

(21) Appl. No.: 15/723,719

(22) Filed: Oct. 3, 2017

(65) Prior Publication Data

US 2018/0095132 A1 Apr. 5, 2018

(30) Foreign Application Priority Data

Oct. 4, 2016 (DE) .................. 10 2016 011 803

(51) Int. Cl.
*G01R 31/34* (2006.01)
*G01N 33/00* (2006.01)
*H02K 33/00* (2006.01)

(52) U.S. Cl.
CPC ......... *G01R 31/34* (2013.01); *G01N 33/0009* (2013.01); *H02K 33/00* (2013.01)

(58) Field of Classification Search
CPC .. H02P 25/06; H02P 2203/03; H02P 29/0241; H02P 29/028; H02P 8/12; H02P 9/009; H02P 9/107; G01R 31/343; G01R 31/34; G01R 31/346; G01R 19/145; G01R 31/06; G06F 11/30; H02M 3/156; H02N 2/163; G01N 33/0009; H02K 33/00
See application file for complete search history.

(56) References Cited

U.S. PATENT DOCUMENTS

| 5,494,343 A | 2/1996 | Lindenmann et al. |
| 6,977,475 B2 * | 12/2005 | Kuribayashi ........... F02N 11/04 290/40 C |
| 7,183,691 B2 * | 2/2007 | Yamamoto .............. H02N 2/142 310/316.01 |

(Continued)

FOREIGN PATENT DOCUMENTS

| DE | 44 19 813 A1 | 12/1995 |
| DE | 10 2004 030309 A1 | 1/2006 |

(Continued)

*Primary Examiner* — Vinh P Nguyen
(74) *Attorney, Agent, or Firm* — McGlew and Tuttle, P.C.

(57) ABSTRACT

A method and a testing device (1) function test a vibration motor (2) arranged in a portable gas-measuring device (3). A sensor (4) detects a value for a motor property transmits the value to a control and analysis unit (5). The detected value is compared with a desired value, a test result is generated on the basis of the comparison, and a trigger signal is generated on the basis of the test result. A terminal voltage and/or current are determined during a switching-on and/or switching-off operation of the vibration motor (2) at an electrical terminal (6) of the vibration motor (2) on the basis of the motor property of the vibration motor (2). This terminal voltage and/or the terminal current present at least at times during the switching-on and/or switching-off operation are compared with at least one desired value in the control and analysis unit (5).

21 Claims, 4 Drawing Sheets (56) References Cited

U.S. PATENT DOCUMENTS

| | | | | |
|---|---|---|---|---|
| 7,573,180 B2* | 8/2009 | Funakubo | ........... | H01L 41/0913 |
| | | | | 310/316.01 |
| 8,531,139 B2* | 9/2013 | Murata | ................. | H02P 25/032 |
| | | | | 318/114 |
| 9,063,105 B2* | 6/2015 | Berndt | ................. | G01N 33/007 |
| 9,128,067 B2* | 9/2015 | Ostermann | ........ | G01N 33/0006 |
| 2004/0108824 A1* | 6/2004 | Ueda | ..................... | H02P 25/032 |
| | | | | 318/114 |
| 2014/0306625 A1* | 10/2014 | Chin | ........................ | H02P 6/08 |
| | | | | 318/128 |
| 2015/0015303 A1* | 1/2015 | Sakurai | ................ | G01R 31/343 |
| | | | | 324/765.01 |
| 2016/0139184 A1* | 5/2016 | Huang | ............... | G01R 19/2503 |
| | | | | 324/120 |

FOREIGN PATENT DOCUMENTS

| | | |
|---|---|---|
| DE | 10 2012 210090 B4 | 1/2014 |
| DE | 10 2013 008425 B3 | 5/2014 |

* cited by examiner

TESTING DEVICE AND METHOD FOR TESTING A VIBRATION MOTOR ARRANGED IN A DEVICE

CROSS REFERENCE TO RELATED APPLICATIONS

This application claims the benefit of priority under 35 U.S.C. § 119 of German Application 10 2016 011 803.2, filed Oct. 4, 2016, the entire contents of which are incorporated herein by reference.

FIELD OF THE INVENTION

The present invention pertains to a testing device as well as to a method for testing a vibration motor arranged in a device. Such a testing device has at least one testing unit, with which at least one value for a property of the vibration motor is detected and transmitted to a control and analysis unit. The detected value is compared in this analysis unit with a desired value, a test result is generated on the basis of the comparison, and a signal, by which a subsequent action is triggered, is generated on the basis of the result.

BACKGROUND OF THE INVENTION

A plurality of testing devices, with which measuring devices are tested automatically for their ability to function properly, are known from the state of the art. Measuring devices are tested by an automatic or semiautomatic method by means of such testing devices in order to ensure that these are still fully functional and there are no safety hazards for the user.

Testing devices, in which portable gas-measuring devices are tested after their use or after the end of a specified time interval, are used especially in the area of portable gas-measuring devices, for example, in production plants in the chemical industry as well as refineries. It is essential here that the sensors used in the portable gas-measuring devices be tested for their ability to function and be calibrated when needed. If a corresponding gas sensor is no longer able to function and must be replaced, corresponding information is outputted via a display unit of the testing device. The components provided for generating an alarm are also likewise tested, as a rule, during a corresponding test.

Such a testing device for portable gas-measuring devices is known, for example, from DE 10 2012 210 090 B4. The testing device has a main unit including a control and analysis unit with a plurality of test modules connected to the main unit for data exchange. A gas-measuring device each can be inserted into a test module, the type of gas-measuring device being detected automatically and the test gas or test gases needed for this type of device being determined on the basis of the detected data. The main unit further has a plurality of gas inlets for different test gases, and the gas is sent to the test module via a gas line under control by the control and analysis unit. The testing device for portable gas-measuring devices specifically has a control and analysis unit, which is configured such that a detailed testing schedule is set up on the basis of the gas-measuring devices located in the testing devices, so that the testing can be carried out in a time-optimized manner in case of a plurality of mobile gas-measuring devices. This is especially significant because the individual gas-measuring devices are always equipped with the respective gas sensors needed based on the need and different test gases are needed for the testing of the different sensors and the duration of the testing of the individual gas-measuring devices may differ.

Further, a testing device for testing mobile gas-measuring devices, which can detect sensor poisonings in the gas-measuring devices in an especially suitable manner, is known from DE 10 2013 008 425 B3. The testing schedule needed for the testing of the individual gas-measuring devices inserted into the testing device is likewise also determined in this testing device on the basis of a corresponding system as well as of a central control and analysis unit. The testing device described is characterized, furthermore, in that a suitable quantity of a test gas is fed to the individual gas-measuring devices in a chronologically spaced manner, and the sensors being tested can be tested based on a comparison of the measured values obtained whether a sensor poisoning is present.

The concentrations of selected gases, which are present in the area surrounding the user of the portable gas-measuring device, who is potentially at risk, are tested with the portable gas-measuring devices, which are routinely tested with the above-described testing devices. Such portable gas-measuring devices therefore also have, in addition to the sensor system necessary for the determination of the gas concentration, suitable output units, which make it possible to generate an alarm for the user of a gas-measuring device. Such an alarm is usually generated both acoustically, optically and/or by touch. Since the portable gas-measuring devices described are frequently used in industrial plants, in which rather substantial noise is generated and/or the user of the device uses a protective device, which makes perception of acoustic signals difficult, modern portable measuring devices have, as a rule, vibration motors, which trigger a vibration alarm in case of an alarm and thus inform the user of the device of a potential hazard.

To also carry out the testing of the vibration motors in portable gas-measuring devices for their ability to function, the humming caused by the vibration was hitherto recorded with a microphone and analyzed during corresponding testing or the vibration activity was tested by means of acceleration sensors. Both of the above-mentioned methods are, however, unreliable and lead to high percentages of false positive or false negative test results.

SUMMARY OF THE INVENTION

Based on the prior-art use of vibration motors in devices, especially in measuring devices, as well as on the above-described problems occurring in connection with the testing of these vibration motors for their ability to function, a basic object of the present invention is to provide a testing device with which reliable testing of the vibration motor can be carried out in a simple manner. In particular, the testing of the vibration motors should be carried out without a considerable effort being needed for this in terms of necessary sensor system as well as analysis. The testing device to be proposed as well as a corresponding method for testing vibration motors should be, on the one hand, highly precise and reliable and, on the other hand, they should minimize the percentage of false positive or false negative test results. Furthermore, it is advantageous if the technical solution to be provided can be integrated in the prior-art testing devices in a comparatively simple manner and without considerable changes in the configuration.

The present invention pertains to testing device for testing a vibration motor arranged in a device, which testing device has a testing unit, with which at least one value for a property of the vibration motor is detected. This detected at least one value for a property of the vibration motor is transmitted to a control and analysis unit, in which the detected value is compared with desired value. A test result is generated on the basis of the comparison, and a signal, by which a subsequent action is triggered, is generated on the basis of the test result. The testing device is characterized according to the present invention in that the testing unit has at least one sensor component for detecting at least one motor-specific measured value, wherein a terminal voltage and/or a terminal current present during a switching-on and/or switching-off operation of the vibration motor on the electrical terminal of the vibration motor is determined on the basis of the motor-specific measured value directly or indirectly as a property of the vibration motor. The terminal voltage present at least at times during the switching-on and/or switching-off operation and/or the terminal current present at least at times during the switching-on and/or switching-off operation are compared with at least one desired value in the control and analysis unit. It is basically irrelevant with respect to the inventive idea whether the testing device is integrated in a mobile gas-measuring device or is part of a testing station, into which the mobile gas-measuring device can be inserted for testing. It is, however, especially advantageous if the testing device configured according to the present invention is an integral part of a mobile gas-measuring device. The measurement and analysis and hence the testing of the gas-measuring device take place in this case directly in this device, so that a corresponding message can be outputted to the user or a signal containing the information can be transmitted to an external unit in this case.

According to an especially preferred embodiment of the present invention, the sensor element has a voltage and/or current-measuring device. The voltage and/or the current on the connection terminal of the vibration motor is measured in this manner directly during the switching-on or switching-off operation and the measured value is compared with a desired value in the control and analysis unit. As an alternative or in addition, a motor speed, especially a rotor speed, of the vibration motor is detected with a speed sensor and is used as the basis for the determination of the terminal voltage and/or of the terminal current during a switching-on or switching-off operation or is compared with a desired value for the speed. An advantageous variant is also conceivable if measured values recorded during the switching-on and/or switching-off operation, i.e., voltage values, current values and/or values of a suitable auxiliary variable are integrated and added up over a time period and the value thus determined is compared with a desired value. It is further conceivable, in general, that at least two values of a voltage, of a current and/or of an auxiliary variable are recorded during a switching-on and/or switching-off operation in order to compare these with corresponding desired values and/or to generate a function curve, which contains these at least two measured values, and to compare the function curve determined with a desired value curve.

It is essential for the technical solution according to the present invention that only the terminal voltage or the terminal current of the vibration motor is monitored during a switch-on phase or switch-off phase rather than the acoustic or mechanical effect of the vibration motor being detected. The ability of the vibration motor to function can be tested from the course of the terminal voltage and/or the terminal current in a simple yet highly precise manner. A vibration motor has, as a rule, a permanently energized shunt generator with a flanged flywheel mass configured as a flyweight. Based on the imbalance, a mechanical vibration and shaking is induced during the rotation of the motor. The basic idea of the present invention is based on utilizing the energy storage property of the inertia of the motor and of the flywheel mass to detect the proper function. The terminal voltage and/or the terminal current are monitored for this reason during the switching-on or switching-off operation. Correct rotation of the motor can be reliably inferred from the time curve and the absolute curve of the terminal voltage and of the terminal current.

When a vibration motor that is able to function is switched on, the terminal voltage has a predictable curve, which is stored as a desired value in a memory connected to the central control and analysis unit. If, by contrast, the vibration motor is blocked, a different terminal voltage curve will appear when the vibration motor is switched on, which can be determined by a comparison of the detected terminal voltage curve with the normal terminal voltage curve being stored in the memory. The behavior of the flywheel mass likewise differs from a normal operation when the vibration motor is switched on as soon as the motor is at least partly blocked. The final speed is not reached immediately when the vibration motor is switched on, but only after a certain time period, the so-called run-up time. The rotation energy is stored during this time in the flywheel mass. If, by contrast, the vibration motor is switched off by the voltage supply to the motor being interrupted, the motor will run until the energy being stored in the flywheel mass is eliminated. The terminal voltage does not immediately collapse to zero in a freely coasting motor, but is only reduced by a certain value $(R_a * J_a)$, because the inert mass continues to maintain the rotation of the rotor and the machine is acting as a generator in this case. Here, $R_a$ is the rotor resistance and $J_a$ is the rotor current. By contrast, the voltage collapses immediately when the motor is blocked.

According to a special embodiment of the present invention, a display unit is provided, on which the test result is displayed as a subsequent action following the testing and the comparison of the terminal voltage and/or of the terminal current. It is essential in this connection that an error message is outputted to the user or to the person in charge of the testing as soon as an inadmissible deviation is detected between the detected terminal voltage and/or the terminal current and the corresponding desired value, from which an at least partial blockage of the vibration motor can be inferred.

In a special variant, the testing device configured according to the present invention for testing a vibration motor arranged in a device has a gas supply, which can be connected to the device, so that at least one gas can be admitted at least at times to a gas sensor arranged in the device. Especially portable gas-measuring devices are monitored with such a testing device both with respect to the correct detection of gas concentrations of at least one gas and the proper function of the vibration motor installed in the gas-measuring device. A portable gas-measuring device is thus preferably tested by means of such a testing device with respect to both the proper function of the sensor system and alarm generation.

The central control and analysis unit of the testing device may be configured such that a device-specific testing schedule is specified on the basis of the detection of the type of the device that is located in a testing device. It is preferably determined within the framework of such a testing schedule whether and to what extent a testing of the vibration motor shall be performed.

Provisions are made according to a special variant for at least one desired value curve, which represents the voltage and/or current curve over a time period, to be provided for the control and analysis unit from a memory for comparison with the detected values for the terminal voltage and/or for the terminal current. According to this variant of the present invention, the at least one desired value stored in a memory is a sequence of a plurality of voltage values or a function curve representing a voltage curve. It is possible in this case to use the respective absolute values of the voltage and of the current that follow one another over time and/or a change in the voltage and/or in the current that takes place during a time period for the comparison of the detected values with the desired value. If function curves for the voltage and/or current curve are stored and these are used for the comparison, it is conceivable to compare the slope of these curves to the slope of the detected voltage or current curves and to output error information in respect to the deviation if an inadmissible limit value is exceeded. A testing device configured according to the present invention for testing a vibration motor arranged in a device is preferably used for testing a vibration motor arranged in a mobile gas-measuring device. It is, of course, equally conceivable to use a testing device configured according to the present invention for testing a vibration motor arranged in a device, with which a time curve of the terminal voltage and/or of the terminal current is monitored during a switching-on and/or switching-off operation of the vibration motor, to test other devices, e.g., general measuring devices or communication devices.

A testing device configured according to the present invention may be integrated in a testing station, to which the measuring device to be tested, which has a vibration motor, can be connected. Such a testing station preferably has a mount, into which the measuring device is inserted or plugged. At least one connection, which make possible a data communication between the testing station and the measuring device, established in this case, so that either information on the terminal voltage and/or the terminal current on the vibration motor during the switching-on or switching-off operation, especially corresponding measured values, is transmitted for analysis to the separate testing station, or, if the analysis is carried out within the testing device, information relating to the state of the vibration motor, especially on whether it operates error-free or incorrectly, is transmitted to the testing station.

The measuring device is preferably a portable gas-measuring device, which can be supplied with at least needed test gas via at least one corresponding gas-tight connection between the testing station and the measuring device. The portable gas-measuring device includes tactile alarm means for generating a tactile alarm. The tactile alarm means comprises the vibration motor.

It is conceivable according to a special embodiment of the present invention that a testing device configured according to the present invention is an integral part of the measuring device to be tested, especially of a portable gas-measuring device. A testing of the vibration motor provided in the measuring device takes place in this case upon a corresponding request by the user and/or automatically after the end of a presettable time period. The terminal voltage and/or the terminal current is detected during the start-up or stopping of the motor following the switching-on or switching-off operation in this case as well, the detected values are compared with stored desired values, and it is determined on the basis of the result of the comparison whether the vibration motor is fully able to function. As soon as an error is detected, this is displayed to the user, especially by means of a light signal or on a display on a device.

Furthermore, the present invention also pertains to a method for testing a vibration motor arranged in a device. When the method is carried out, at least one value for a property of the vibration motor is detected, the detected value is compared with at least one desired value, a test result is generated on the basis of the comparison, and a signal, by which a subsequent action is triggered, is generated on the basis of the test result. The variant of the method according to the present invention is characterized by the steps of—detecting a terminal voltage and/or a terminal current at the electrical terminal of the vibration motor during a switching-on and/or switching-off operation of the vibration motor, and—comparing a time curve of the terminal voltage and/or of the terminal current with the at least one desired value.

According to a special variant according to the present invention of the method, absolute values of a voltage and/or of a current intensity or a change in a voltage and/or in a current intensity within a time period are used as a desired value. Furthermore, provisions are advantageously made for sending an error message to a display, to a memory and/or to an external data receiver as soon as a deviation between detected values of the terminal voltage and/or of the terminal current and at least one desired value exceeds or drops below a permissible limit value.

It is likewise conceivable in this connection that a corresponding message is also transmitted to a central monitoring system, as it is used, for example, in large chemical plants, refineries or drilling rigs. Provisions are also made according to a special variant of the present invention for the terminal voltage and/or the terminal current to be detected at at least two times or over a time period during the switching-on and/or switching-off operation of the vibration motor. The present invention will be explained in more detail below without restriction of the general inventive idea on the basis of exemplary embodiments with reference to the figures. In the drawings, The present invention will be described in detail below with reference to the figures attached. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
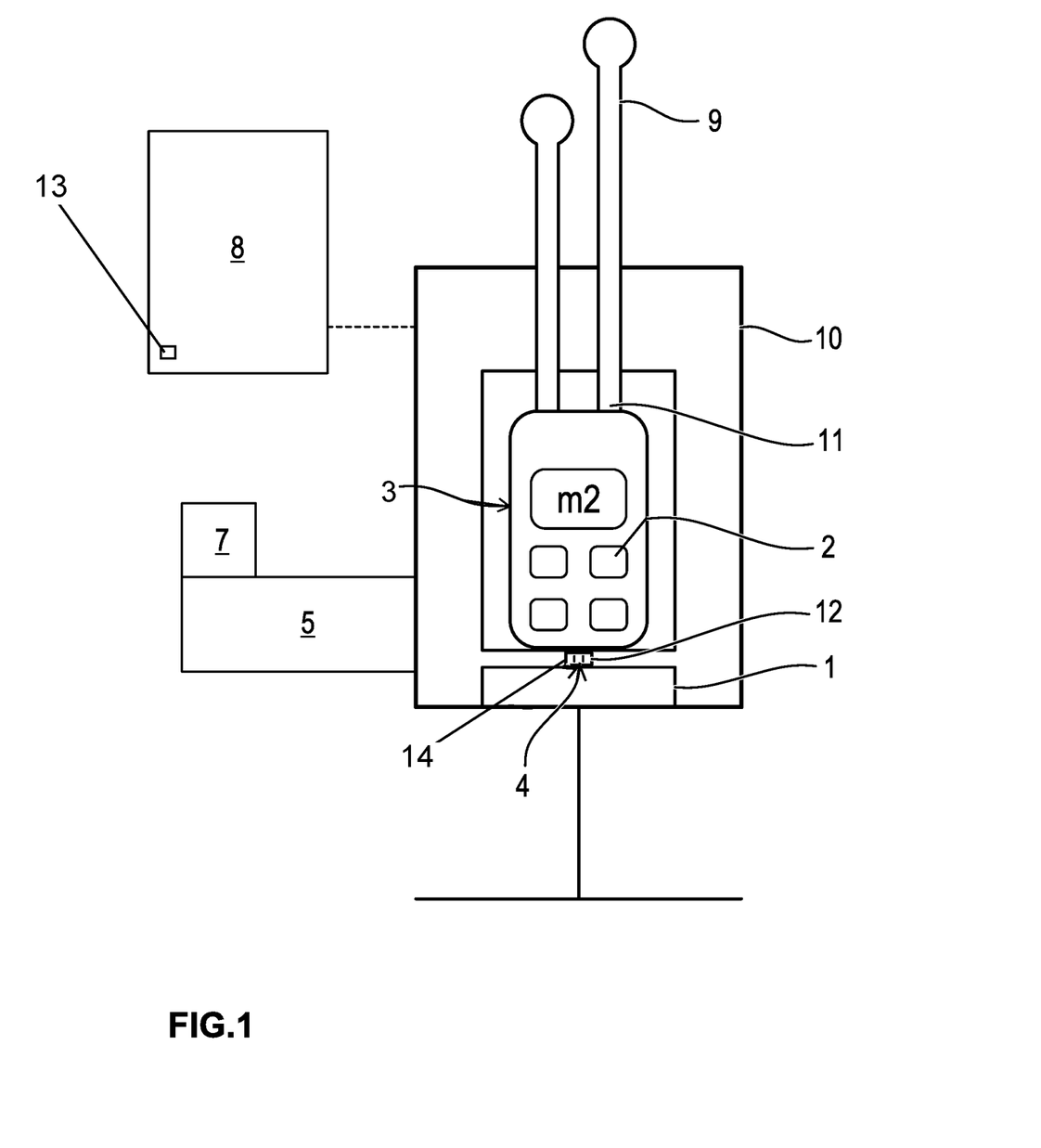
FIG. 1 is a schematic view of a testing device configured according to the present invention for testing a vibration motor installed in a device for proper function.

Referring to the drawings, FIG. 1 shows a schematic view of a testing device 1 configured according to the present invention for testing the ability of a vibration motor 2, which is arranged at a device 3, here a portable gas-measuring device, to function. The portable gas-measuring device 3 is located in a testing module 10 of the testing device 1 and is connected, on the one hand, to a test gas supply 9 of the testing device 1 via suitable gas ports 11. Further, contacts are provided as an electrical interface 12, via which the terminal voltage at the electrical terminal 6 of the vibration motor 2 can be detected. The testing device 1 has a sensor component 4 for this, which is configured according to this embodiment as a current- and/or voltage-measuring unit. The sensor component 4 may be a tachometer 14. The portable gas-measuring device 3 includes a tactile alarm means for generating a tactile alarm. The tactile alarm means comprises the vibration motor 2.

After the identification of the gas-measuring device 3 inserted into the test module 10 has taken place, which is carried out, as desired, by means of a manual input or by automated identification of the device 3 on the basis of a suitable code, the central control and analysis unit 5 of the testing device 1 determines a device-specific testing schedule.

On the one hand, the type and number of the gas sensors provided in the portable gas-measuring device 3 and, on the other hand, the voltage curves on the connection terminals 6, which curves are specific of the vibration motor 2 installed in the device 3 during the start-up and stopping operation, are stored in this device-specific testing schedule. The testing of the gas sensors will not be discussed in detail below. Reference is made in this connection to the solutions known from the state of the art, as they are disclosed, among other things, in the documents cited in the introduction to the specification. Further, the testing device 1 may be configured according to the present invention as an integral part of the measuring device 3. According to this embodiment the test device 1 is integrated into the device to be tested 3. In this case the measuring device 3 is a portable gas-measuring device and includes the control and/or analysis unit 5 and a memory 7 (although the gas connection 9 is not required). The memory 7 includes a data receiver 13. The portable gas-measuring device 3 includes a tactile alarm means for generating a tactile alarm. The tactile alarm means comprises the vibration motor 2. The portable gas-measuring device 3 with the integrated features may include a display as shown.

Figure 2A:
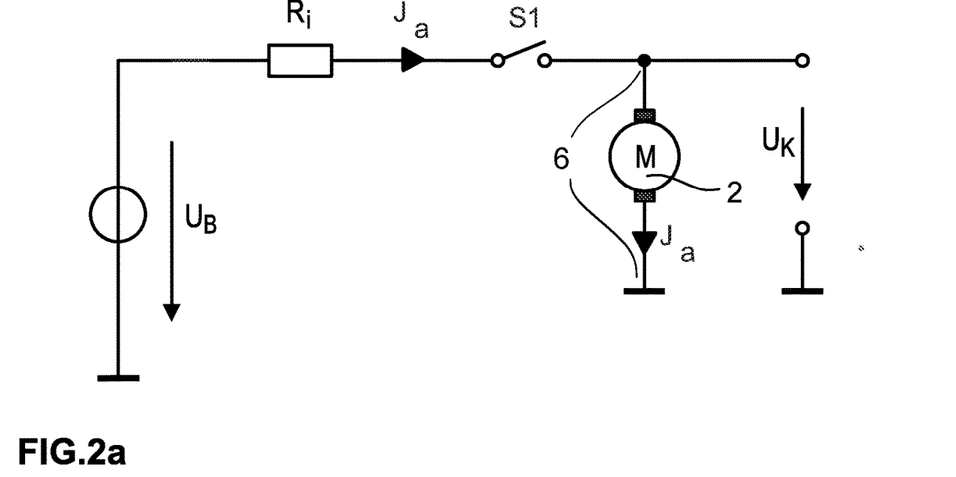
FIG. 2a is a circuit diagram with a vibration motor, which is connected to a voltage source via a switch and a resistor, which are connected in series.

FIG. 2a shows a circuit diagram with the vibration motor 2, which is connected to a voltage source via a switch and a resistor, which switch and resistor are connected in series. The vibration motor 2 is supplied here from a d.c. voltage source $U_B$, which has an internal resistance $R_i$.

Figure 3:
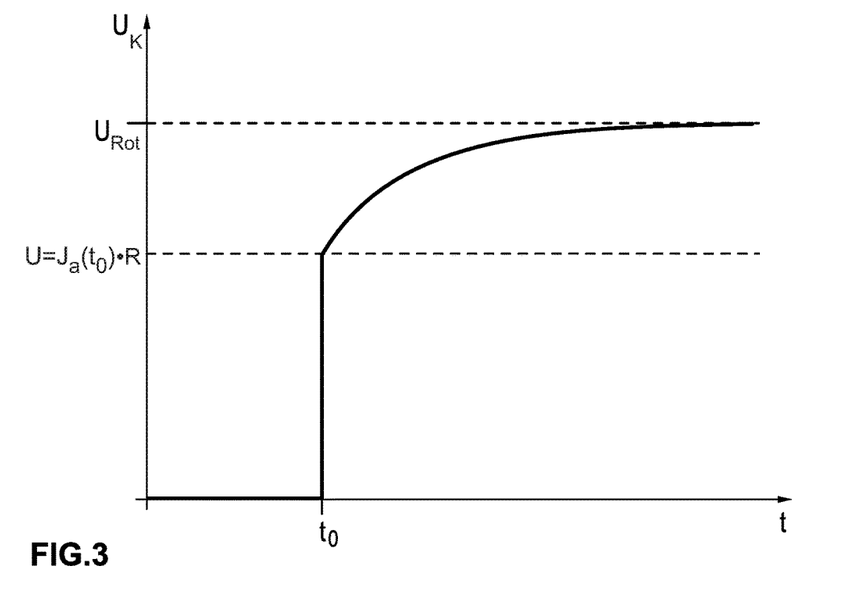
FIG. 3 is the terminal voltage curve of a freely running vibration motor during a switching-on operation.
Figure 4:
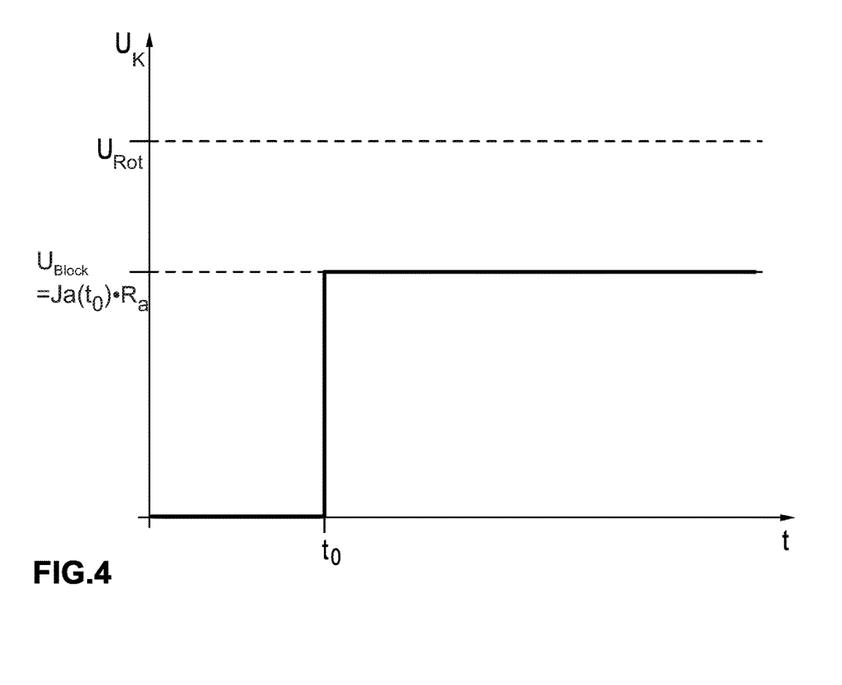
FIG. 4 is a terminal voltage curve of a blocked vibration motor during a switching-on operation.

The voltage $U_B$ and the rotor current $J_a$ as well as the terminal voltage $U_K$ of the motor are detected for the analysis. With the motor running, the voltage curve $U_K(t)$ shown in FIG. 3 is obtained. The rotor current $J_a(t_0)$ is calculated in this case to be $J_a(t_0)=U_B/(R_i+R_a)$. The terminal voltage accordingly increases from $J_a(t_0)*R_a$ to the substantially higher value $U_{Rot}$ which is close to $U_B$. With the motor blocked, the voltage curve $U_K(t)$ shown in FIG. 4 is obtained. The terminal voltage $U_K$ jumps in this case to the value $U_{Block}=J_a(t_0)*R_a$ and then remains at least approximately equal. The rotor current $J_a$ is calculated to be $J_a(t_0)=U_B/(R_i+R_a)$.

Figure 2B:
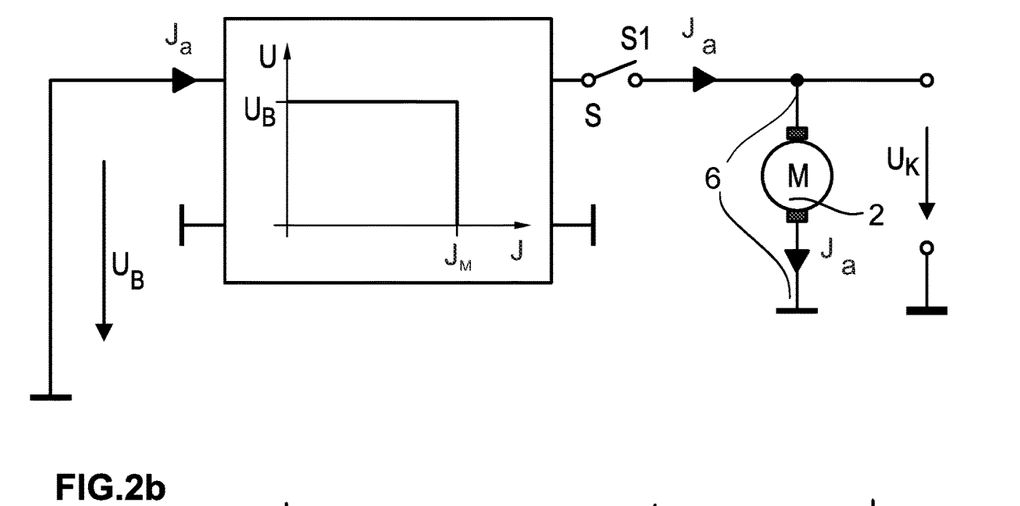
FIG. 2b is a circuit diagram with a vibration motor, which is connected to a voltage source via a switch and an electronic current limiter, which are connected in series.

FIG. 2b shows a circuit diagram with the vibration motor 2, which is connected to a voltage source via a switch and is connected to an electronic current limiter, which switch and electronic current limiter are connected in series. According to this embodiment, the motor 2 is supplied from an electronically current-limited d.c. voltage source. The voltage $U_B$, the rotor current $J_a$ as well as the terminal voltage $U_K$ of the motor are likewise detected for the analysis.

With the motor running freely, the voltage curve $U_K(t)$ shown in FIG. 3 is obtained in this case as well. The rotor current $J_a(t_0)$ is calculated in this case to be $(t_0)=U_B/R_a$ or, if $U_B/R_a>=I_M$, to be $J_a(t_0)=I_M$. The terminal voltage accordingly rises from $J_a(t_0)*R_a$ to the substantially higher value $U_{Rot}$, which is close to $U_B$. With the motor blocked, the voltage curve shown in FIG. 4 is obtained. The terminal voltage $U_K$ jumps to the value $U_{Block}=J_a(t_0)*R_a$ and then remains at least approximately the same; the rotor current $J_a$ is calculated to be $J_a(t_0)=U_B/R_a$ or, if $U_B/R_a>=I_M$, to be $J_a(t_0)=I_M$. $U_K$ remains at $U_{Block}$.

Figure 2C:
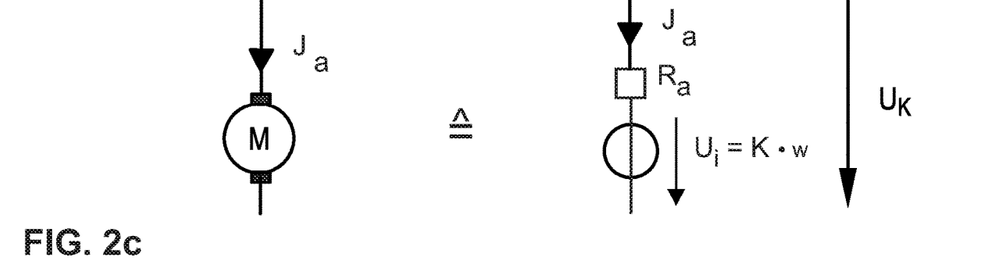
FIG. 2c is a view of a vibration motor and of an equivalent circuit diagram.

FIG. 2c shows the vibration motor M as well as the equivalent circuit thereof. This equivalent circuit comprises a voltage source $U_i$ and an ohmic resistor $R_a$, which represents the Cu (copper) resistor of the rotor winding. The rotor inductance, which is present as well, may be ignored. $U_i$ represents the cumulated voltage generated by the rotation, which is directly proportional to the speed w in a first approximation, and $U_i=K_m*w$ applies. To test the vibration motor 2 for its ability to function properly, the central control and analysis unit 5 first generates a control signal, so that a voltage is present on the connection terminals 6 of the vibration motor 2 and the switching-off operation is triggered. The vibration motor 2 is now run up to its operating speed. If the vibration motor 2 is fully able to function, i.e., it is not blocked, the terminal voltage will assume the curve shown in FIG. 2.

With a vibration motor 2 running up freely, a corresponding voltage curve of the terminal voltage, as is shown in FIG. 3, is detected, it is compared in the central control and analysis unit 5 with a desired voltage curve, which had been sent to the control and/or analysis unit 5 from a memory 7, and no or only a slight deviation, which is below a permissible limit value, is detected if the vibration motor 2 is not blocked.

A signal is now generated in the control and analysis unit 5 on the basis of this comparison and is transmitted to the display unit 8 of the testing device 1, which display unit is configured as a display, where it is displayed that the vibration motor 2 of the portable gas-measuring device 1 tested is fully able to function.

Should the vibration motor 2 of the gas-measuring device 1 to be tested be blocked at least partly, the terminal voltage curve shown in FIG. 4 will become established during the run-up of the vibration motor 2. This voltage curve is characterized above all by an abrupt rise in the terminal voltage, the voltage jump taking place at the moment at which the supply voltage is switched on. An inadmissible deviation is detected in this case during the testing of the terminal voltage curve and during the comparison of the detected terminal voltage curve with the stored desired voltage curve by the control and analysis unit 5, and the output of an error message on the display unit 8 or on the display of the testing device 1 is correspondingly initiated.

The user now obtains information that the vibration motor 2 provided in the tested measuring device 1 is at least partly blocked.

Figure 5:
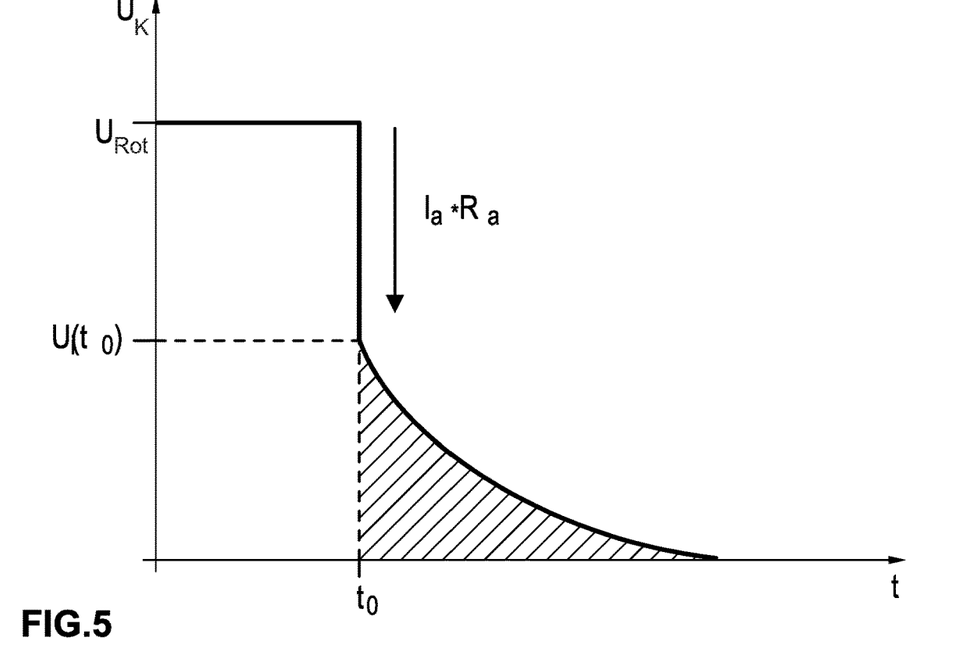
FIG. 5 is a terminal voltage curve of a freely running vibration motor during a switching-off operation.

As an alternative or in addition, the testing of the vibration motor 2 may be carried out during a switching-off operation. If a freely running vibration motor 2 is switched off, terminal voltage curves as shown in FIG. 5 are obtained. With the vibration motor 2 running freely, the terminal voltage $U_K$ present on the connection terminals 6 does not collapse immediately to zero, but it decreases by the value $R_a*J_a$, i.e., the product of the winding resistance $R_a$ by the intensity $J_a$ of the current flowing in this area. Based on its insert mass, the rotor of the vibration motor 2 still continues to rotate at first, so that the vibration motor 2 acts as a generator during this phase. This is the cause of the comparatively slow voltage drop.

Figure 6:
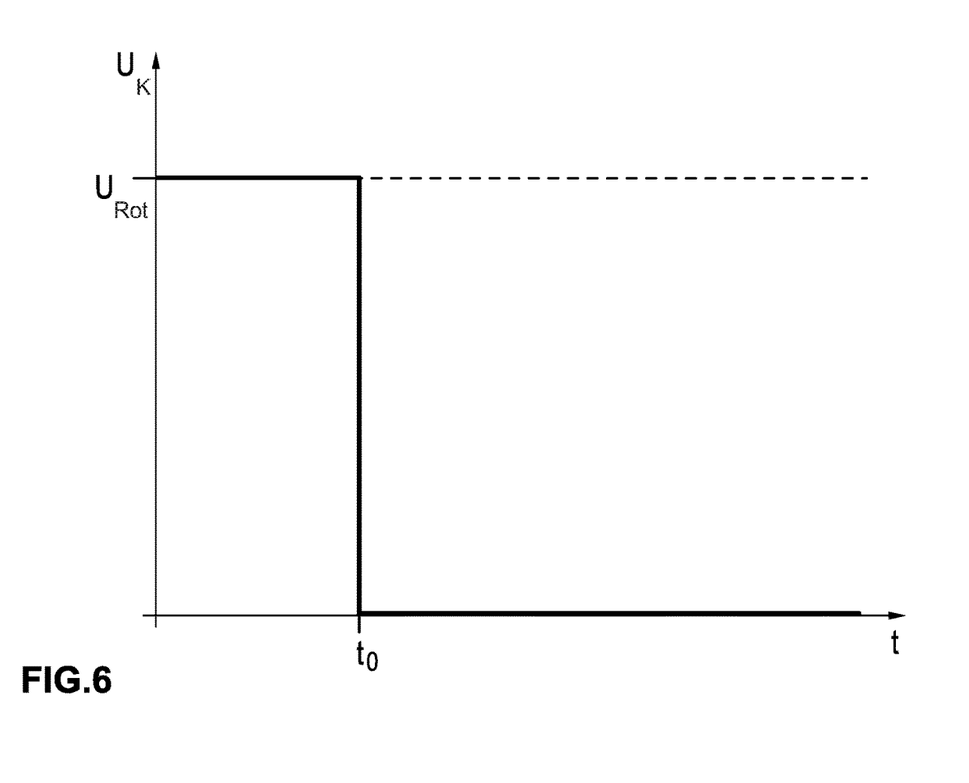
FIG. 6 is a terminal voltage curve of a fully blocked vibration motor during switching-off operation.

If, by contrast, the vibration motor is blocked at least partly, the voltage curve shown in FIG. 6 is obtained on the connection terminals 6 of the vibration motor. It now becomes clear that the voltage on the connection terminals 6 collapses or is reduced to zero at the moment at which the rotor with its flywheel mass is blocked. Regardless of whether the voltage is the voltage applied during the switching-on operation or the voltage induced during the switching-off operation, the detection of the voltage and/or of the voltage curve on the connection terminals 6 is carried out by individual or multiple measurement or by forming the integral of the recorded voltage curve.

It is likewise conceivable that a plausibility check is performed by analyzing a quasi-static measurement. If the vibration motor 2 starts running, the terminal voltage $U_K$ on the connection terminals 6 must always be higher than the value for $[U_B*R_a/(R_a+R_i)]$, where $U_B$ is the operating voltage, $R_a$ is the rotor voltage and $R_i$ is the internal resistance of the supply voltage source.

Other plausibility checks are preferably also possible, in which case the induced voltage on the connection terminals 6, which was detected during the switching-off operation, is analyzed. It can thus be stated in summary that the testing device 1 configured according to the present invention makes possible a simple and at the same time reliable testing of a vibration motor 2 installed in a device 3, especially in a measuring device. It is essential here for the technical solution according to the present invention that the voltage or the current detected on the connection terminals 6 of the vibration motor 2 during a switching-on or switching-off operation is compared with a device-specific desired value, which occurs during undisturbed operation of the vibration motor 2. The testing device 1 configured according to the present invention may be integrated here either in the device 3, for example, a portable gas-measuring device, itself, so that the device can perform a self-test, or it may be a part of as testing module 10, which is connected to the device 1 and tests and/or calibrates the vibration motor 2 and possibly additional components of the device 1, for example, installed sensors.

It is further conceivable, in general, to detect, in addition or as an alternative to the measurement of the terminal voltage on the vibration motor 2 during the switching-on or switching-off operation, auxiliary variables, for example, the motor speed or the rotor speed and to determine therefrom the voltage present on the connection terminal 6 and/or the current in the analysis and control unit 5. The terminal voltage or the terminal current are not measured directly in this manner, but they are determined indirectly on the basis of at least one suitable auxiliary variable, and the corresponding values are sent to the control and analysis unit. It is conceivable, in principle, in this connection to send suitable auxiliary variables for a plausibility check or to determine the terminal voltage and/or the terminal current during a switching-on or switching-off operation of the vibration motor exclusively by means of such auxiliary variables.

While specific embodiments of the invention have been shown and described in detail to illustrate the application of the principles of the invention, it will be understood that the invention may be embodied otherwise without departing from such principles.

APPENDIX

List of Reference Designations

1 Testing device
2 Vibration motor
3 Device
4 Sensor component
5 Control and analysis unit
6 Electrical terminal of the vibration motor
7 Memory
8 Display unit
9 Gas supply
10 Test module
11 Gas port
12 Electrical interface between the testing device and the device

What is claimed is:

1. A testing device for testing a vibration motor arranged in a device to be tested, the testing device comprising:
a testing unit comprising a sensor component for detecting at least one motor-specific measured value for a property of the vibration motor of the device, the device being a mobile gas-measuring device, wherein a terminal voltage and/or a terminal current, determined directly or indirectly at an electrical terminal of the vibration motor during a switching-on and/or switching-off operation of the vibration motor, is detected as the property of the vibration motor, the testing device being part of the gas-measuring device or the testing device being part of a testing station into which the gas-measuring device is configured to be inserted for testing; and
a control and analysis unit with a memory associated therewith, the memory having at least one desired value, the control and analysis unit being configured to compare the terminal voltage present at least at times during the switching-on and/or switching-off operation and/or the terminal current present at least at times during the switching-on and/or switching-off operation with the at least one desired value.

2. A testing device in accordance with claim 1, wherein the sensor component comprises a voltage- and/or current-measuring device, the testing unit comprising an interface, the sensor component being configured to detect the at least one motor-specific measured value for the property of the vibration motor with the device to be tested connected to the interface, the control and analysis unit determining whether the vibration motor is in one of a correct functioning state and an incorrect functioning state based on a comparison of the terminal voltage present at least at times during the switching-on and/or switching-off operation and/or the terminal current present at least at times during the switching-on and/or switching-off operation with the at least one desired value.

3. A testing device in accordance with claim 1, wherein the sensor component comprises a tachometer to detect a motor speed of the vibration motor.

4. A testing device in accordance with claim 1, wherein the control and analysis unit is configured such that the terminal voltage and/or the terminal current is integrated during the switching-on and/or switching-off operation over a time period and the value obtained is compared with the desired value.

5. A testing device in accordance with claim 1, further comprising a display unit, on which a test result is displayed as an action subsequent to the comparison.

6. A testing device in accordance with claim 1, further comprising a gas supply with a gas connection from the gas supply to the mobile gas-measuring device to be tested so that at least one gas can be admitted to a gas sensor arranged in the device to be tested.

7. A testing device in accordance with claim 1, wherein at least two desired values for the terminal voltage and/or for the terminal current detected during a switching-on and/or switching-off operation and/or a function curve containing the two desired values are provided for the control and analysis unit from the memory for comparison with the detected terminal voltage and/or with the detected terminal current.

8. A testing device in accordance with claim 1, wherein the at least one desired value represents an absolute value, an integral or a change in a voltage and/or in a current intensity.

9. A testing device method comprising:
providing a testing device for testing a vibration motor arranged in a device to be tested, the testing device comprising a testing unit comprising a sensor component for detecting at least one motor-specific measured value for a property of the vibration motor, wherein a terminal voltage and/or a terminal current, determined directly or indirectly at an electrical terminal of the vibration motor during a switching-on and/or switching-off operation of the vibration motor, is detected as the property of the vibration motor and a control and analysis unit with a memory associated therewith, the memory having at least one desired value, the control and analysis unit being configured to compare the terminal voltage present at least at times during the switching-on and/or switching-off operation and/or the terminal current present at least at times during the switching-on and/or switching-off operation with the at least one desired value; and
connecting the device to be tested with the testing device, wherein the device to be tested is a portable gas-measuring device for generating a tactile alarm.

10. A method for testing a vibration motor arranged in a device, the method comprising the steps of:
detecting at least one value for a property of the vibration motor of the device, the device being a mobile gas measuring device;
comparing the detected at least one value with at least one desired value; and
generating a test result based on the comparison and generating a signal, by which a subsequent action is triggered based on the test result, wherein a terminal voltage and/or a terminal current is determined at an electrical terminal of the vibration motor during a switching-on and/or switching-off operation of the vibration motor as the detected at least one value for a property of the vibration motor and the step of comparing compares a time curve of the terminal voltage and/or of the terminal current with the at least one desired value.

11. A method for testing a vibration motor according to claim 10, wherein the steps of detecting, comparing and generating are performed with a testing device for testing the vibration motor arranged in the mobile gas measuring device to be tested, the testing device comprising a testing unit comprising an interface and a sensor component for detecting at least one motor-specific measured value for a property of the vibration motor, wherein a terminal voltage and/or a terminal current, determined directly or indirectly at an electrical terminal of the vibration motor during a switching-on and/or switching-off operation of the vibration motor, is detected as the property of the vibration motor with the device connected to the interface of the testing device and a control and analysis unit with a memory associated therewith, the memory having at least one desired value, the control and analysis unit being configured to compare a value of the terminal voltage present at least at times during the switching-on and/or switching-off operation and/or the terminal current present at least at times during the switching-on and/or switching-off operation with the at least one desired value, the test result providing an indication of whether the vibration motor is operating in one of a correct functioning state and an incorrect functioning state.

12. A method in accordance with claim 10, wherein the terminal voltage and/or the terminal current is detected during the switching-on and/or switching-off operation as the motor-specific measured value.

13. A method in accordance with claim 10, wherein a motor speed is measured as the motor-specific measured value and is based as the basis for the determination of the terminal voltage and/or of the terminal current during the switching-on and/or switching-off operation.

14. A method in accordance with claim 10, wherein an absolute value, an integral and/or a change in a voltage, in a current intensity and/or in an auxiliary variable, on which the determination of the terminal voltage and/or of the terminal current is based as the value and is compared to a corresponding desired value.

15. A method in accordance with claim 10, wherein an error message is sent to a display to a memory and/or to an internal data receiver as soon as a deviation of the determined terminal voltage and/or of the determined terminal current from the at least one desired value exceeds or drops below a permissible limit value.

16. A method in accordance with claim 10, wherein the terminal voltage and/or the terminal current is determined at at least two times or during a time period during the switching-on and/or switching-off operation of the vibration motor.

17. A mobile gas-measuring device comprising:
a vibration motor;
a gas sensor arranged in the mobile gas-measuring device; and
a testing device integrated with the mobile gas-measuring device, the testing device comprising:
a testing unit comprising a sensor component for detecting at least one motor-specific measured value for a property of the vibration motor, wherein a terminal voltage and/or a terminal current, determined directly or indirectly at an electrical terminal of the vibration motor during a switching-on and/or switching-off operation of the vibration motor, is detected as the property of the vibration motor; and a control and analysis unit with a memory associated therewith, the memory having at least one desired value, the control and analysis unit being configured to compare the terminal voltage present at least at times during the switching-on and/or switching-off operation and/or the terminal current present at least at times during the switching-on and/or switching-off operation with the at least one desired value.

18. A mobile gas-measuring device in accordance with claim 17, wherein the sensor component comprises a voltage- and/or current-measuring device or a tachometer to detect the motor speed, the control and analysis unit being configured to compare the terminal voltage present at least at times during the switching-on and/or the switching-off operation and/or the terminal current present at least at times during the switching-on and/or switching-off operation with the at least one desired value to a provide a comparison of values, wherein the control and analysis unit determines whether the vibration motor is functioning in one of a correct state and an error state based on the comparison of values.

19. A mobile gas-measuring device in accordance with claim 17, wherein the control and analysis unit is configured such that the terminal voltage and/or the terminal current is integrated during the switching-on and/or switching-off operation over a time period and the value obtained is compared with the desired value.

20. A mobile gas-measuring device in accordance with claim 17, wherein at least two desired values for the terminal voltage and/or for the terminal current detected during a switching-on and/or switching-off operation and/or a function curve containing the two desired values are provided for the control and analysis unit from the memory for comparison with the detected terminal voltage and/or with the detected terminal current.

21. A mobile gas-measuring device in accordance with claim 17, further comprising tactile alarm means for generating a tactile alarm, the tactile alarm means comprising the vibration motor.

* * * * *